(12) United States Patent
Geurts (10) Patent No.: US 12,060,313 B2
(45) Date of Patent: Aug. 13, 2024

(54) UREA PRODUCTION PROCESS AND PLANT WITH PARALLEL MP UNITS

(71) Applicant: STAMICARBON B.V., Sittard (NL)

(72) Inventor: Wilhelmus Hubertus Geurts, Born (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/007,232

(22) PCT Filed: Feb. 22, 2022

(86) PCT No.: PCT/NL2022/050095
§ 371 (c)(1),
(2) Date: Jan. 27, 2023

(87) PCT Pub. No.: WO2022/177438
PCT Pub. Date: Aug. 25, 2022

(65) Prior Publication Data
US 2023/0265051 A1    Aug. 24, 2023

(30) Foreign Application Priority Data
Feb. 22, 2021    (EP) ..................... 21158449

(51) Int. Cl.
*B01J 10/00*        (2006.01)
*B01J 19/00*        (2006.01)
*C01C 1/18*         (2006.01)
*C07C 273/04*       (2006.01)

(52) U.S. Cl.
CPC ............. *C07C 273/04* (2013.01); *B01J 10/00* (2013.01); *B01J 19/0053* (2013.01); *B01J 19/0086* (2013.01); *C01C 1/185* (2013.01); *B01J 2219/00006* (2013.01); *B01J 2219/0002* (2013.01); *B01J 2219/00038* (2013.01); *B01J 2219/00761* (2013.01)

(58) Field of Classification Search
CPC ................... B01J 19/0053; B01J 10/00; B01J 2219/00761; B01J 2219/00038; B01J 2219/0002
See application file for complete search history.

(56) References Cited

U.S. PATENT DOCUMENTS

| 4,801,745 A | 1/1989 | Meessen et al. |
| 5,767,313 A | 6/1998 | Jonckers |
| 10,759,745 B2 | 9/2020 | Pustjens et al. |
| 2004/0116743 A1 | 6/2004 | Mennen |

(Continued)

FOREIGN PATENT DOCUMENTS

| CN | 101166715 A | 4/2008 |
| CN | 101591269 A | 12/2009 |

(Continued)

OTHER PUBLICATIONS

Meessen, Ullmann's Encyclopaedia, chapter Urea, 2010. 39 pages.

(Continued)

*Primary Examiner* — Lessanework Seifu
(74) *Attorney, Agent, or Firm* — Leason Ellis LLP (57) ABSTRACT

Some embodiments of the disclosure pertain to a plant and a process for producing a urea-containing product. The plant comprises a medium pressure dissociation unit and a high pressure $CO_2$ stripper each receiving a part of the urea synthesis solution. Stripped urea solution is further treated in a medium pressure treatment unit.

22 Claims, 1 Drawing Sheet

(56) References Cited

U.S. PATENT DOCUMENTS

| | | |
|---|---|---|
| 2009/0062566 A1 | 3/2009 | Kojima |
| 2009/0292140 A1 | 11/2009 | Zardi et al. |
| 2012/0302789 A1 | 11/2012 | Mennen |
| 2015/0119603 A1 | 4/2015 | Van Den Tillaart et al. |
| 2019/0359558 A1 | 11/2019 | Sa |
| 2020/0306663 A1 | 10/2020 | Poppa |
| 2021/0331086 A1 | 10/2021 | Dobree et al. |

FOREIGN PATENT DOCUMENTS

| | | |
|---|---|---|
| CN | 102906067 A | 1/2013 |
| CN | 103819365 A | 5/2014 |
| CN | 111295370 A | 6/2020 |
| EP | 0212744 A1 | 3/1987 |
| EP | 3274297 A1 | 1/2018 |
| EP | 3541780 A1 | 9/2019 |
| WO | 2011157530 A1 | 12/2011 |
| WO | 20130165246 A1 | 11/2013 |
| WO | 2016085343 A1 | 6/2016 |
| WO | 2016099269 A1 | 6/2016 |
| WO | 2019083367 A1 | 5/2019 |
| WO | 2020130817 A1 | 6/2020 |

OTHER PUBLICATIONS

International Search Report for corresponding International Application No. PCT/NL2022/050095, dated May 19, 2022.
Chinese First Office Action in CN Application No. 202280016068.1, mailed Dec. 14, 2023, an English translation is attached hereto (10 pages).

UREA PRODUCTION PROCESS AND PLANT WITH PARALLEL MP UNITS

CROSS-REFERENCE TO RELATED PATENT APPLICATIONS

This application is a U.S. National Stage Application under 35 U.S.C. § 371 of International Patent Application No. PCT/NL2022/050095 filed Feb. 22, 2022, which claims the benefit of priority of European Patent Application No. 21158449.5 filed Feb. 22, 2021, both of which are incorporated by reference in their entireties. The International Application was published on Aug. 25, 2022, as International Publication No. WO/2022/177438 A1.

FIELD

The invention pertains to the production of urea from $NH_3$ and $CO_2$.

INTRODUCTION

Urea plants are often of the type with a high pressure (HP) stripper, for instance with a high pressure (HP) stripper using at least part of the $CO_2$ feed as strip gas (e.g. the Stamicarbon $CO_2$ stripping process). An example process scheme of a urea process of the $CO_2$-stripping type is shown in Ullmann's Encyclopaedia, chapter Urea, 2010, FIG. 16. The HP stripper is operated with a stripping efficiency of e.g. 80% and has a corresponding demand for steam as heating fluid.

US 2004/0116743A1 mentions that the HP stripping step and the HP condensation step are largely responsible for the fact that it is only to a limited extent possible to expand the capacity of an existing facility without modification or replacement of expensive high-pressure equipment. US '743 proposes increasing the capacity of a plant by modifying the plant such that a part of the urea synthesis solution is transferred from the synthesis zone to a medium-pressure treatment zone operated at a pressure of 1-4 MPa; the other part is sent to the HP stripper. US '743 illustrates plants wherein the medium-pressure treatment zone comprises a medium pressure carbamate condenser MCC receiving a gas stream from a medium pressure dissociator and a gas stream from a medium pressure stripper. The medium pressure stripper receives liquid from the medium pressure dissociator and a part of the $CO_2$ feed. The medium pressure dissociator receives liquid directly from the urea reactor. The stripped urea solution from the high pressure stripper is supplied directly to a low pressure recovery section.

EP 3274297 describes an integrated system for the production of urea and urea ammonium nitrate, said system comprising (i) a unit for the production of urea, said unit comprising a urea synthesis section comprising a reactor, a stripper and a condenser in fluid communication with each other so as to form a urea synthesis loop, and, downstream of the synthesis section and in fluid communication therewith, a urea purification section suitable for separating off $CO_2$ and $NH_3$ from an aqueous urea solution comprising said $CO_2$ and $NH_3$, and (ii) a unit for the production of ammonium nitrate from ammonia and nitric acid; wherein an outlet for $NH_3$ from the purification section of the urea plant is connected to an inlet for $NH_3$ of the unit for the production of ammonium nitrate, and wherein an outlet for an aqueous urea solution from the purification section and an outlet for an aqueous ammonium nitrate solution from the unit for the production of ammonium nitrate, are connected to a unit for mixing said aqueous urea solution and said aqueous ammonium nitrate solution.

EP 3541780 describes an integrated process for the production of urea and urea-ammonium nitrate.

US 2012/0302789A1 describes a urea production process with a HP $CO_2$ stripper wherein the urea solution leaving the stripper is subjected to an adiabatic expansion, thus creating a vapor and a liquid, which are separated before the liquid enters a first recovery section and the vapor is condensed.

$CO_2$ emissions from industrial plants are often limited for environmental reasons or require emission permits, even if emission allowances are tradable any $CO_2$ emissions may increase cost.

There remains a desire for an energy efficient urea production process, in particular for large scale plants. There is also a desire for process for the integrated production of urea and ammonium nitrate with low $CO_2$ emissions and with low energy consumption. There is also a desire for corresponding plants and methods of modifying existing plants. The invention is not limited to process for the integrated production of urea and ammonium nitrate and also includes embodiments wherein only urea is produced. Desired energy savings may be achieved in preferred embodiments. Improved energy efficiency and integrated production of urea and ammonium nitrate are preferred objectives of some but not necessarily all embodiments of the invention.

SUMMARY

The invention pertains in a first aspect to a plant for producing a urea-containing product, the plant comprising a urea production section comprising a high pressure (HP) synthesis section comprising a HP stripper, a reactor for forming urea from $NH_3$ and $CO_2$, and a HP carbamate condenser, wherein the reactor and the HP carbamate condenser are optionally combined, the urea production section further comprising a medium pressure (MP) treatment unit, an MP dissociator and an MP condensation section, wherein the reactor has an outlet for a urea synthesis solution connected to a first liquid flow line connected to the HP stripper, wherein said outlet is also connected to a second liquid flow line connected to the MP dissociator, wherein the HP stripper has an inlet for $CO_2$ feed as strip gas, wherein the plant comprises a liquid flow line for stripped urea solution from said HP stripper to said MP treatment unit, a gas flow line for a first MP gas stream from the MP treatment unit to the MP condensation section, and a gas flow line for a second MP gas stream from the MP dissociator to the MP condensation section.

Preferably the plant further comprises a low pressure (LP) dissociator and a liquid flow line for MP urea solution from the MP treatment unit to said LP dissociation.

Preferably the plant comprises an ammonium nitrate (AN) section comprising a neutralization section configured for neutralizing nitric acid with ammonia to form ammonium nitrate and having an inlet for nitric acid and an inlet for ammonia-containing gas. Preferably the plant comprises a gas flow line for ammonia-containing LP gas from said preferred LP dissociator to said neutralization section.

The invention further pertains to a process for producing a urea-containing product carried out in a plant according to said first aspect, the process comprising: reacting $NH_3$ feed and $CO_2$ feed in said reactor, to give a urea synthesis solution; dividing said urea synthesis solution in at least a first part and a second part; supplying said first part to said HP stripper thereby obtaining stripped urea solution; subjecting said stripped urea solution to treatment at medium pressure in said MP treatment unit giving said first MP gas stream; subjecting said second part to medium pressure dissociation in said MP dissociator to give said second MP gas stream and MP urea solution, and supplying said first and second MP gas stream at least in part to said MP condensation section.

The invention also pertains to a method of modifying an existing plant for producing a urea-containing product. Preferably the existing plant comprises a urea production section comprising a high pressure (HP) synthesis section comprising a HP stripper, a reactor for forming urea from $NH_3$ and $CO_2$, and a HP carbamate condenser, wherein the reactor and the HP carbamate condenser are optionally combined, wherein the HP stripper has an inlet for $CO_2$ feed as strip gas. The method comprises adding an MP dissociator and an MP condensation section, and a connection from the outlet for a urea synthesis solution to the MP dissociator, if not already present in the existing plant. The method also comprises adding a medium pressure (MP) treatment unit, and a liquid flow line for stripped urea solution from said HP stripper to said MP treatment unit, a gas flow line for a first MP gas stream from the MP treatment unit to the MP condensation section, and a gas flow line for a second MP gas stream from the MP dissociator to the MP condensation section, if the gas flow line for a second MP gas stream is not already present in the plant. The modified plant is preferably a plant according to the first aspect of the invention.

BRIEF DESCRIPTION OF THE DRAWINGS

Any embodiments illustrated in the figures are examples only and do not limit the invention.

DETAILED DESCRIPTION

The urea production plant and process of the present disclosure are broadly based on the judicious insight of using an MP dissociator receiving urea synthesis solution from the reactor, and an MP treatment unit receiving stripped urea solution from a HP stripper, wherein at least a gas stream from the MP dissociator and a gas stream from the MP treatment unit are supplied directly or indirectly to an MP condensation section. In said MP condensation section the gas streams are at least in part condensed to yield a carbamate solution. In particular, the gas stream from the MP dissociator is condensed at least in part in the MP condensation section and the gas stream from the MP treatment unit is condensed at least in part in said MP condensation section, preferably said gas streams are both condensed at least in part in the same condenser, wherein the condenser is e.g. a heat exchanger.

Supplying a gas stream from the MP treatment unit to the MP condensation section may advantageously contribute to less $CO_2$ emissions from one or more units downstream of the outlet for liquid (i.e. for urea solution) of the MP treatment unit. Supplying a gas stream from the MP treatment unit to the MP condensation section may contribute the condensation of carbamate in the MP condensation section at an advantageous N/C ratio.

By supplying a gas stream from the MP treatment section to the MP condensation section advantageously relatively more $CO_2$ may be recycled as part of the MP carbamate solution to the HP synthesis section. Thereby $CO_2$ recovery is improved and emissions from the preferred ammonium nitrate (AN) section are reduced.

Advantageously steam consumption of the HP stripper may be reduced by virtue of the MP treatment unit processing the urea solution supplied to that MP treatment unit.

Compared to a process wherein the MP condensation section receives only gas from the MP dissociator and MP $CO_2$ feed, advantageously more $CO_2$ can be sent to the HP stripper. This may further contribute to lower steam consumption of the HP stripper. Lower steam consumption of the HP stripper is generally desirable and contributes to higher energy efficiency of the plant.

The size of the HP stripper can advantageously be relatively small compared to the total urea production capacity in the inventive plant.

The MP dissociator and the MP treatment unit are arranged in parallel in the plant.

The HP synthesis section comprises a HP stripper, a HP reactor and a HP carbamate condenser. The stripper is a $CO_2$ stripper. The plant comprises a first liquid flow line from the reactor to the HP stripper and a second liquid flow line from the reactor to the MP dissociator. The HP synthesis section comprises an inlet for $NH_3$ feed, for example at the HP carbamate condenser.

The reactor is configured for forming urea from $NH_3$ and $CO_2$ and has an outlet for urea synthesis solution. The urea synthesis solution e.g. has an N/C ratio of 2.85 to 3.3. The reactor is operated at urea synthesis pressure, i.e. HP, and urea synthesis temperature, e.g. above 100 bar, for instance 120 to 300 bar, e.g. 120 to 200 bar; and/or for instance at a temperature of 160-240° C. and preferably at a temperature of 170-220° C.

The reactor is for instance a vertical reactor with trays, wherein the feed inlet is at the bottom and the urea synthesis solution is withdrawn from an upper part of the vertical reactor, for instance using a down-comer.

The reactor for instance has a separate outlet for gas (so-called inerts). The inerts are supplied for instance as gas stream directly or indirectly to the preferred AN section. The inerts originate e.g. from the feed streams and include e.g. $N_2$. The gas stream from the gas outlet of the reactor comprises e.g. also $NH_3$.

The urea production plant may comprise one or more reactors in series, for instance a first reactor and an after-reactor. The after-reactor receives e.g. the reactor effluent and has a liquid outlet connected to the split between the first and second flow line, i.e. the first and second liquid flow line. The urea production plant may also comprise one or more reactors in parallel.

The reactor and the HP carbamate condenser are optionally combined in a single vessel. An example is an integrated reactor/condenser as described in U.S. Pat. No. 5,767,313. An example integrated condenser/reactor comprises a reaction zone and a condensation zone combined in a single vessel. The condensation zone comprises for instance a heat exchanging surface, such as a tube bundle. The reaction zone comprises for instance baffles. The reaction zone is typically arranged downstream of the condensation zone in the vessel. An example integrated condenser/reactor comprises a horizontal vessel and a tube bundle configured for receiving cooling fluid in the tubes and process medium in the shell space.

The reactor has an outlet for a urea synthesis solution connected, directly or indirectly, to a first liquid flow line to the HP stripper, and to a second liquid flow line to the MP dissociator. The second liquid flow line bypasses the HP stripper. The plant comprises a split of the HP urea synthesis solution flow line into the first and second flow line, using e.g. a valve. Typically the plant plant comprises a split, i.e. a divider, of a flow line for HP urea synthesis solution into said first liquid flow line and said second liquid flow line. The flow line for HP urea synthesis solution is connected to the outlet for urea synthesis solution of the reactor. The splitting or dividing of the urea synthesis solution is performed at high pressure. The first and second liquid flow line both are used for a liquid stream at HP. The second liquid flow line connected to the MP dissociator typically contains an expansion valve for expanding the urea solution from HP to MP.

The split ratio of the HP urea synthesis solution can preferably be adjusted e.g. during start-up or to increase or decrease urea production in a flexible way. For example, the MP dissociator can be turned down for lower urea production.

The urea synthesis solution comprises urea, water, ammonium carbamate and ammonia.

The HP stripper has an inlet for $CO_2$ feed as strip gas and has an outlet for stripped urea solution, and an outlet for a gas stream. The plant is preferably of the $CO_2$ stripping type. The stripped urea solution comprising urea, water, carbamate and ammonia, and is supplied to the MP treatment unit.

The HP carbamate condenser (HPCC) typically receives at least a part, preferably all, of the raw $NH_3$ feed. The HPCC receives at least a part, for instance all, of the gas stream from the HP stripper. The HP carbamate condenser has an outlet for a stream comprising the condensed carbamate connected to an inlet of the reactor, and in a combined condenser/reactor the condensation zone is in fluid connection with the reaction zone.

The urea production section may comprise a $CO_2$ compressor to compress a $CO_2$ feed stream to urea synthesis pressure. The compressor is for instance a multi-stage compressor. The $CO_2$ is for example available at relatively low pressure (e.g. less than 20 bar) at battery limit, e.g. from a synthesis gas plant. The synthesis gas plant comprises for example a steam reformer, a water gas shift reactor, and a $CO_2$ removal unit. The synthesis gas plant may also produce $H_2$ used in an ammonia plant. The $NH_3$ feed of the urea plant may originate from said ammonia plant. Other sources of the $CO_2$ feed stream and $NH_3$ feed stream are also possible.

Generally, in the various embodiments of the invention, the HP stripper comprises for example a vertical shell-and-tube heat exchanger with an inlet for supplying urea solution to be stripped into the tubes, said inlet provided at the top of the stripper, and an outlet for stripped urea solution at the bottom, and an outlet for a mixed gas stream at the top of the stripper. The HP stripper is of the $CO_2$ stripping type and has an inlet for $CO_2$ feed used as strip gas at the bottom. The mixed gas stream is condensed in the HP carbamate condenser into a high pressure recycle stream containing carbamate which is supplied to the reactor. In case of a combined reactor/condenser in a single vessel this may involve transport of condensate from a condensation section to a reactor section inside the vessel, in particular flow of carbamate-containing liquid from a condensation zone to a reaction zone inside the vessel.

The HP stripper is typically a device configured for counter-current contact of urea solution with a strip gas stream. Typically the HP stripper is configured with the urea solution and the strip gas stream in the tubes, while heat is supplied by steam on the shell side. In the invention, the HP stripper uses all or a part of the raw $CO_2$ feed as strip gas. The stripping action with $CO_2$ as strip gas causes a reduction of the N/C ratio of the urea solution. The stripped urea solution has an N/C ratio that is lower than the urea synthesis solution, e.g. an N/C ratio of less than 3.0, less than 2.7 or even less than 2.5, such as in the range 1.5-2.5 or in the range 2.0-2.5.

In preferred embodiments wherein a liquid outlet for MP carbamate solution of the MP condensation section is connected to a liquid flow line to the HP synthesis section, thereby providing for recycle of carbamate solution to the HP synthesis section, the HP stripper is for instance operated with a stripping efficiency a in the range of 60-80%, for example 65-75%, e.g. stripping efficiency a of about 70%. In embodiments where carbamate solution from the MP condensation section is disposed of in other ways, e.g. by supplying the solution to an additional urea synthesis section, the stripping efficiency may be e.g. in the range of up to 92%.

Advantageously, the HP stripper can be operated with relatively low stripping efficiency by virtue of the MP treatment unit receiving the stripped urea solution and used for purification of that urea solution, thereby providing for a relatively low steam consumption in the HP stripper.

In the plants and processes of the invention, the HP carbamate condenser (HPCC) is for instance a shell-and-tube heat exchanger. The HPCC is for instance a vertical condenser or a horizontal condenser. A shell-and-tube heat exchanger as HPCC is operated with process medium (in particular, the gas to be condensed) in the shell side space and cooling fluid in the tubes, or with process medium in the tubes and cooling fluid in the shell side space.

In some embodiments, the HPCC is for instance a falling-film carbamate condenser with cooling fluid in the shell. In further embodiments, the HPCC is for instance a submerged condenser. The HPCC is for instance a shell-and-tube condenser with a horizontal U-shaped tube bundle, process medium in the shell side and with a submerged tube bundle, and is e.g. a pool condenser. The HPCC comprises e.g. a U-shaped tube bundle or a straight tube bundle. The HPCC is optionally a pool reactor, which comprises a pool condenser zone and a reactor zone. The pool reactor comprises for instance baffles in the shell space.

The HPCC for example also comprises an inlet for $NH_3$ feed to the shell space.

The MP treatment unit is configured for subjecting the stripped urea solution to a treatment comprising expansion to MP and gas/liquid separation to give the first MP gas stream and first MP urea solution, and optionally also comprising heating. In some embodiments, the MP treatment is substantially adiabatic or is adiabatic. In some embodiments the MP treatment unit has an inlet for a gas stream, such as a $CO_2$ feed stream, and the treatment in the MP treatment unit optionally involves contacting the urea solution with a gas stream, with or without heating.

The treatment in the MP treatment unit provides for the purification of the stripped urea solution by removal of at least some $NH_3$ and $CO_2$ from the solution and/or decomposition of carbamate into $NH_3$ and $CO_2$ and removal of $NH_3$ and $CO_2$ from the solution to give a first MP gas stream. The first MP gas stream comprises $NH_3$ and $CO_2$.

In some optional embodiments, counter-current contacting the stripped urea solution in the MP treatment unit with a part of the $CO_2$ feed stream is used. This contacting is optionally combined with heating the urea solution in the MP treatment unit.

For instance, heating the stripped urea solution in the MP treatment unit, operated at MP, using e.g. indirect heat exchange with a heating fluid, e.g. steam, may contribute to more complete removal of $NH_3$ and ammonium carbamate from the stripped urea solution.

Removal of ammonium carbamate from the stripped urea solution in the MP treatment unit may contribute to reduced $CO_2$ emissions from an AN neutralization section coupled to the urea production section. Thereby $CO_2$ recovery is improved by the MP treatment unit and the supply of the first MP gas stream to the MP condensation section.

Preferably, the MP treatment unit is configured for flashing of the urea solution, more preferably (substantially) adiabatic flashing. In some embodiments, the MP treatment unit is an MP flash vessel.

Advantageously, by the preferred (substantially) adiabatically flashing from HP to MP in an MP flash vessel (MPF) the first MP gas stream has a low $NH_3:CO_2$ molar ratio, such as lower than 2.0, e.g. in the range 0.8-1.2, and/or lower than the N/C ratio of the HP stripped urea solution. The first MP gas stream may advantageously have a relatively high $CO_2$ concentration such that the MP condensation section may operate at a more advantageous N/C ratio.

In some embodiments, $NH_3$ and $CO_2$ are removed from the urea solution in the MP flash vessel in a molar ratio $NH_3$ to $CO_2$ of less than 2.0, such as a molar ratio in the range of 0.8-1.2. The first MP gas stream may have an even lower molar ratio $NH_3$ to $CO_2$ if $CO_2$ is added to the gas stream.

The MP treatment unit comprises a gas/liquid separation zone, e.g. in the preferred flash vessel, e.g. by the zone or the flash vessel having a top outlet for gas and a bottom outlet for liquid, wherein the liquid is urea solution.

The MP treatment unit is for instance used for expanding the urea solution from high pressure to medium pressure, e.g. to a pressure of for example 10-50 bar, e.g. 15-40 bar. The MP treatment unit is operated at e.g. a pressure at least 1.0 bar higher, for instance 2-10 bar higher than the pressure of the MP condensation section.

The preferred adiabatic nature of the flash in the preferred MP flash vessel advantageously contributes to a low N/C ratio (molar ratio $NH_3$ to $CO_2$) of the formed gas stream. In particular, upon adiabatic pressure reduction $CO_2$ leaves the urea solution from the $CO_2$ HP stripper to a higher degree than $NH_3$.

The first MP gas stream has an N/C molar ratio (molar ratio $NH_3$ to $CO_2$) of preferably less than 2.0, e.g. 0.5-1.5, such as 0.9-1.2, e.g. about 1.0. The first MP gas stream contains $NH_3$ and $CO_2$ in a molar ratio of preferably less than 2.0, e.g. 0.5-1.5, such as 0.9-1.2, e.g. about 1.0. The first gas stream contains for instance about 40-50 wt. % $NH_3$, about 40-50 wt. % $CO_2$, and e.g. 10-20 wt. % $H_2O$; these ranges may also apply to the components removed from the liquid phase of the urea solution in case of $CO_2$ being added to the first MP gas stream. The first gas stream as received by the MP carbamate condenser, i.e. at the inlet of the condenser, preferably has such N/C molar ratio (molar ratio $NH_3$ to $CO_2$), and preferably contains for instance about 40-50 wt. % $NH_3$, about 40-50 wt. % $CO_2$, and e.g. 10-20 wt. % $H_2O$.

The MP dissociator (MPD) has an inlet connected to the second liquid flow line for receiving a part of the urea synthesis solution and an outlet for a second MP gas stream and an outlet for MP urea solution. The MP is typically a heat exchanger using a heating fluid, for example steam, for indirect heat exchange for dissociating carbamate that is comprised in the urea synthesis solution. The use of steam as heating fluid in the MP dissociator provides the advantage of great flexibility to ensure sufficient carbamate removal from the urea solution, in particular independently of the N/C ratio at the inlet of the of the MP dissociator. The MP dissociator is for instance a shell-and-tube heat exchanger with steam in the shell and urea solution in the tubes. The MP dissociator comprises for instance a rectifying section arranged, for urea solution, upstream of the shell-and-tube heat exchanger part, the rectifying section being configured for gas/liquid separation of the urea solution expanded from HP to MP and counter-current contact between urea solution and a gas stream from the heat exchanging part. This contributes to good removal of carbamate from the urea solution.

The MP urea solution at the outlet of the MP dissociator has for instance an N/C ratio of at least 4. The second MP gas stream from the MP dissociator has for instance an N/C ratio of at least 2.5.

In some embodiments, the MP dissociator also receives other urea solution streams, such as urea solution obtained indirectly from the HP stripper.

The MP dissociator is e.g. a shell-and-tube heat exchanger, and e.g. uses steam as heating fluid. For instance, the MP dissociator is a vertical shell-and-tube heat exchanger with urea solution in the tubes and with a rectifying unit on top.

The second MP gas stream is supplied from the MP dissociator to the MP condensation section (MPCC). The MP condensation section has a liquid outlet for carbamate solution.

The plant comprises a gas flow line for the first MP gas stream from the MP treatment unit directly or indirectly, preferably directly, to the MP condensation section such that at least part of said gas, preferably all, is transported as gas to the MP condensation section. In this way advantageously $CO_2$ contained in the stripped urea solution may be recovered using the MP condensation section.

In embodiments with the preferred (substantially) adiabatic flash, at least a part of the vapor from the flash can be used to correct (decrease) the N/C ratio in the MP condensation section. The combined carbamate condensation of the first and second MP gas stream in the MP condensation section provides for optimum N/C ratio close to 2 of the formed condensate, i.e. carbamate solution. Thereby recovery of $CO_2$ in the form of carbamate solution is enabled. The carbamate condensation is also advantageously achieved at relatively higher temperature (higher condensation point) with the advantageous relatively low N/C ratio in the MP condensation section.

By virtue of the MP treatment unit, the $CO_2$ comprised in the first MP gas stream from the MP treatment unit, which $CO_2$ originates from the HP stripper, can be used and recovered in the MP condensation section, such that the steam consumption of the HP stripper may be lower at constant stripping efficiency a. Thereby relatively more $CO_2$ can be supplied advantageously to the HP stripper. In preferred embodiments with an ammonia-consuming unit, e.g. the ammonium nitrate section, the HP stripper may advantageously operate with relatively lower stripping efficiency a compared to urea production sections only producing urea melt as $NH_3$ included in the stripped urea solution (also as carbamate) and received by the preferred LP dissociator can be used in the preferred ammonia-consuming unit, e.g. be reacted in the preferred ammonium nitrate section. The skilled person understands that in the context of urea plants, a lower stripping efficiency a, as that term is used in the art, can provide an advantage.

The MP condensation section comprises one or more MP carbamate condensers and has a liquid outlet for MP carbamate solution connected for instance to a recycle flow line to the HP synthesis section. The MP condensation section also comprises an outlet for non-condensed gas. The gas is supplied e.g. to an absorber or scrubber, or for instance to a neutralization section of the optional AN section. Typically, the plant comprises only a recycle flow line from an MP unit to the HP synthesis section for carbamate solution. Typically, the plant does not include an ammonia condenser and does not include a dedicated recycle flow line for ammonia to the HP synthesis section.

The MP condensation section may comprise an MP carbamate condenser operated with a cooling fluid, e.g. a cooling liquid, such as cooling water, optionally as second MP carbamate condenser arranged downstream of a first MP carbamate condenser, wherein the first condenser is for instance heat integrated with a pre-evaporator, as discussed hereinafter. The second condenser is for instance a shell-and-tube heat exchanger. The second condenser receives for instance both vapor and liquid from the first MP carbamate condenser. The MP condensation section further comprises a gas/liquid separator, in particular for separating the carbamate solution from the non-condensed gas.

The MP condensation section preferably receives an aqueous stream, e.g. ammonia water, e.g. an aqueous stream from a waste water treatment section or for instance steam condensate. Thereby crystallization of carbamate is advantageously avoided. Optionally the MP condensation section receives for instance LP carbamate solution from an optional LP carbamate condenser if used.

Optionally, at least one condenser in the MP condensation section (MPCC) is in heat exchanging contact through a heat exchanging wall with an optional pre-evaporator (PEV) which is used for concentrating urea solution, for instance urea solution received directly or indirectly from an LP dissociator as discussed hereinbefore and hereinafter, by water evaporation by heating to give concentrated urea solution and a vapor stream. The carbamate condensation is exothermic. This provides advantageously for heat integration.

The pre-evaporator comprises for instance a heat exchanging section and a gas/liquid separation section. The urea solution in the pre-evaporator is for instance at 0.4-0.6 bar absolute.

The term 'pre-evaporator' as used herein does not imply that a further evaporator must be used. For instance, the concentrated urea solution may be used as such, for instance for making UAN (urea ammonium nitrate liquid fertilizer). The concentrated urea solution may also be further concentrated to provide e.g. a urea melt and the plant may comprise an evaporation section for further concentrating the urea solution from the pre-evaporator.

The MP condensation section, in particular the first MP condenser, is for instance provided at least in part by a heat exchanger having a heat exchanging wall and a first and a second zone which are in heat exchanging contact with each other through said wall, with MP process fluids in the first zone, in particular the first and second MP gas stream to be condensed, and urea solution in the second zone. The MP condensation section is for instance provided at least in part by a shell-and-tube heat exchanger with MP process medium in the shell and urea solution in the tubes, in particular as said first MP condenser. The second zone is operated e.g. at lower pressure than the first zone. The heat exchange advantageously provides for heat integration.

The advantageously relatively low N/C ratio in the MPCC permits for carbamate condensation at relatively high temperature and contributes to efficient water evaporation in the pre-evaporator by the heat integration.

Preferably the MP urea solution from the MP dissociator is expanded to LP and preferably heated at LP, with gas/liquid separation in an LP treatment unit (such as an LP dissociator), to further purify the urea solution by removal of ammonia and/or carbamate, giving an LP urea stream and an LP gas stream. The expansion to LP and the heating at LP is for instance carried out in a dedicated LP treatment unit or in the same LP treatment unit as used for treating urea solution downstream of the liquid outlet of the MP treatment unit.

The plant accordingly preferably comprises a, low pressure (LP) dissociator, a LP carbamate condenser, a flow line, e.g. liquid flow connection, for urea solution from said MP dissociator to said LP dissociator, optionally through the MP stripper, and a gas flow line from said LP dissociator to said LP carbamate condenser.

The LP gas stream is for instance condensed to an LP carbamate stream in an LP carbamate condenser, or is for instance supplied as ammonia-containing gas stream to an ammonia-consuming unit, for instance to a neutralization unit, for example a neutralization unit of the preferably used AN section.

Preferably the plant comprises low pressure (LP) dissociator, a LP carbamate condenser, a flow line for urea solution from the MP dissociator to the LP dissociator, and a gas flow line from the LP dissociator the LP carbamate condenser. Preferably, the plant comprises an MP stripper, preferably for adiabatic MP stripping, having an inlet for urea solution from said MP dissociator, an inlet for a $CO_2$-comprising gas stream, e.g. MP $CO_2$ feed and/or gas from the MP flash vessel, an outlet for stripped MP urea solution and an outlet for a gas stream connected to the MP condensation section, Preferably the plant comprises a liquid flow line for the stripped MP urea solution from the MP stripper to the LP dissociator. Details of the MP stripper are discussed hereinafter.

The urea synthesis solution from the reactor is divided in at least two parts, with a first part of for instance 50-90 vol. % supplied to the HP stripper and a second part of e.g. 10-50 vol. % supplied to the medium pressure dissociator (percentages based on total volume of the urea synthesis solution). Advantageously, this ratio can be adjusted thereby increasing the flexibility of the plant, e.g. with a valve provided in the flow line for urea synthesis solution. For instance in periods of lower demand, total urea production may be decreased by supplying less urea synthesis solution to the MP treatment section. The ratio is optimized in such a way that the recycle stream from the MP and LP sections to the synthesis is minimized. This leads to less water in the synthesis section, resulting in a more efficient urea synthesis.

In some embodiments the urea production process is operated during at least some periods with at least 30 vol. % or at least 40 vol. % of the urea synthesis solution supplied to the MP dissociator.

The division of the urea synthesis solution is carried out e.g. in a flow divider comprised in the HP synthesis section and at HP.

In some embodiments, a part of the $CO_2$ feed of the urea productions section is supplied directly or indirectly as MP feed $CO_2$ stream to the MP condensation section.

In preferred embodiment, the amount of MP feed $CO_2$ stream to the MP condensation section is less than 70%, or less than 60%, and e.g. more than 10%, of the amount of $CO_2$ comprised in the first MP gas stream. Thereby a significant part of the $CO_2$ supplied to the MP condensation section comes from the MP treatment unit processing urea solution from the HP stripper, wherein preferably the processing is adiabatic MP flashing.

The MP feed $CO_2$ stream is for instance obtained from the $CO_2$ compressor of the urea plant or from battery limit. In some embodiments, the $CO_2$ compressor is a multi-stage compressor and the additional $CO_2$ stream is extracted optionally from an intermediate stage of the compressor. In some embodiments the MP feed $CO_2$ stream is obtained from a dedicated MP $CO_2$ compressor.

In an interesting optional embodiment, urea solution from the MP dissociator is subjected to counter-current direct contact with a gas stream, for example with a $CO_2$ gas stream and/or with the first MP gas stream from the MP treatment unit, with or without heating, preferably without heating, in an MP stripper. This optional contacting may provide for a stripping effect, in particular for stripping of $NH_3$ from the urea solution. Stripping without heating at MP can be referred to as adiabatic MP stripping. MP solution is subjected to the counter-current direct contact, i.e. at MP.

The gas stream used for the optional MP adiabatic stripping is for instance the first MP gas stream and/or an MP feed $CO_2$ stream. In some embodiments, only MP feed $CO_2$ stream is used for the optional MP adiabatic stripping. In some embodiments, a variable combination of MP flash vapor and MP feed $CO_2$ stream is used for the optional MP adiabatic stripping. In the optional MP adiabatic stripper the gas used for stripping is for example in counter-current direct contact with the urea solution.

If used, the MP stripper is for example configured for adiabatic stripping of the urea solution from the MP dissociator by contacting said urea solution directly with a gas stream, for example with the first MP gas stream, and gas/liquid separation to give a gas stream that is supplied to the MPCC, and stripped MP urea solution that is supplied to a low pressure section, for example to an LP dissociator.

The optional MP stripper for instance comprises a packed bed for said gas/liquid contacting.

In the optional MP stripper, the N/C ratio of the urea solution is decreased e.g. from about 6 to about 3 (example values only). Accordingly the MP stripper provides for a decrease of the N/C ratio, similarly to a high pressure $CO_2$ stripper in the HP synthesis section.

The term 'stripping' is used for the optional MP stripper to broadly indicate that the gas/liquid contacting therein contributes to a decrease of the N/C ratio. The MP stripping may for instance involve absorption of some $CO_2$ into the liquid and transfer of some $NH_3$ from the liquid phase into the gas phase. The liquid at the outlet is e.g. 90-110 wt. % of the liquid at the inlet. The optional MP adiabatic stripping does not necessarily involve a large mass decrease of the liquid phase.

For example embodiments with such an optional MP stripper, the plant for instance further comprises a low pressure (LP) dissociator, an LP carbamate condenser, a liquid flow line for urea solution from the MP stripper to said LP dissociator, and a gas flow line from said LP dissociator to said LP carbamate condenser. These LP units can also be used without the optional MP stripper, in that case the plant comprises a liquid flow line for urea solution from the MP dissociator directly or indirectly to the LP dissociator. The LP dissociator receiving urea solution directly from the MP dissociator can be the preferred LP dissociator receiving urea solution directly or indirectly from the MP treatment unit and indirectly from the HP stripper, or an additional LP dissociator.

The LP dissociator downstream of the MP dissociator, with or without the optional MP stripper, has for example a gas outlet connected to a gas inlet of an ammonia-consuming unit, such as the described neutralization unit of a nitric acid plant.

The urea synthesis solution is rich in ammonia (e.g. N/C of at least 3.0) such that the second MP gas stream from the MP dissociator is also rich in ammonia. For condensation of this gas into carbamate at MP in the MP condensation section the N/C ratio advantageously is adjusted (decreased) for instance to avoid excess $NH_3$ and/or to provide for greater flexibility, e.g. for processing a relatively large fraction of the urea synthesis solution in the MP dissociator. In the present invention, very advantageously the first MP gas stream, e.g. from the preferred MP flash, may be used for this adjustment of the N/C ratio. This may provide for a larger part, or even all, of the raw $CO_2$ feed being introduced into the urea plant and process at high pressure, in particular in the HP stripper, thereby improving the HP stripper efficiency and the urea yield and/or reducing energy consumption, compared to reference processes wherein only raw feed $CO_2$ is used for said N/C adjustment in the MP condensation section. In embodiments with the preferred AN section, $CO_2$ emissions from the AN section are also advantageously reduced by the $CO_2$ recovery through the MP treatment unit and the MP condensation section.

Bypassing of part of the urea synthesis solution around the HP stripper to the MP treatment section, allows for a single line (single train) urea plant with large urea capacity without the stripper becoming too heavy and/or too large for construction and for transport.

The urea production section yields urea solution, e.g. LP urea solution. The urea solution may e.g. be used in part or entirely for producing liquid fertilizer such as UAN, and for other purposes. The urea solution may e.g. also be used in part or entirely for producing urea melt in an evaporation section. The urea melt may be used e.g. in part or entirely for producing solid urea in a finishing section, for example as granules or prills. The urea melt may be used e.g. in part or entirely for producing melamine Combinations of these uses are also possible.

Aspects of the invention pertain to a plant for producing a urea-containing product.

Preferably the plant further comprises an ammonia-consuming unit comprising an inlet for ammonia-containing gas from a unit comprised in said urea production section downstream of the outlet for urea solution of the MP treatment unit. For example the ammonia-consuming unit has an outlet for gas to be vented and in operation $CO_2$ comprised in the one or more gas streams received by the unit is vented at least in part or entirely through said outlet.

Preferably the plant further comprises an ammonium nitrate section comprising a neutralization section configured for neutralizing nitric acid with ammonia to form ammonium nitrate and having an inlet for nitric acid and an inlet for ammonia-containing gas from a unit comprised in said urea production section downstream of the outlet for urea solution of the MP treatment unit. For example the neutralization section or the ammonium nitrate section has an outlet for gas to be vented and in operation $CO_2$ comprised in the one or more gas streams received by the neutralization section is vented at least in part or entirely through said outlet.

In some embodiments, at least one of the urea-containing products comprises urea and an ammonium salt, e.g. ammonium nitrate. The invention also pertains to a plant for the production of urea and ammonium nitrate, e.g. a plant for producing at least UAN (urea ammonium nitrate) liquid fertilizer. In some embodiments the plant has UAN as only product. In some embodiments the plant produces multiple urea-containing products.

In a particular embodiment, urea solution from the MP treatment unit is treated in an LP dissociator giving LP urea solution and ammonia-containing LP gas, which gas is for instance supplied to an ammonia-consuming unit, for instance an ammonium nitrate (AN) plant, in particular to supply part or all of the ammonia used for neutralization of an acid, e.g. for neutralization of nitric acid into ammonium nitrate in said AN section. The LP dissociator and/or additional LP dissociator has for instance a gas outlet that is in gas flow connection with a gas inlet of the neutralization section.

In these embodiments, the plant is a plant for the integrated production of urea and ammonium nitrate and the process is a process for the integrated production of urea and ammonium nitrate. Optionally a part or all of the urea product, e.g. all or part of the LP urea solution from at least one LP dissociator, is combined with ammonium nitrate to form urea ammonium nitrate (UAN) solution which can be used e.g. as fertilizer. Also in these embodiments, an optional second part of the urea product may be used e.g. as feed for a melamine plant, or for instance be supplied to a finishing section for producing solid urea product.

In embodiments with an AN section, the LP section is for instance operated at 1.10-3.0 bar absolute, such as about 1.5 bar absolute. The relatively low pressure contributes to better $NH_3$ removal in the LP dissociator. The neutralization section of the AN section operates e.g. at atmospheric pressure.

Advantageously, the MP treatment unit contributes to relatively lower $CO_2$ emissions from the AN section. In this way additionally the load of the HP $CO_2$ compressor (of the $CO_2$ feed to the HP stripper) is reduced.

The invention also pertains to a process for producing a urea-containing product carried out in the inventive plant as discussed hereinbefore and hereinafter. The process comprises for example reacting $NH_3$ feed and $CO_2$ feed in said reactor, to give a urea synthesis solution. The urea synthesis solution is divided in at least a first part and a second part, preferably using the split ratio as described hereinbefore. The first part is supplied to the HP stripper thereby obtaining stripped urea solution. The stripped urea solution is subjected to treatment at medium pressure in the MP treatment unit to remove one or more components other than urea from the solution giving said first MP gas stream and MP urea solution having a higher concentration of urea. The second part is subjected to medium pressure dissociation in said MP dissociation to give said second MP gas stream and MP urea solution. The process further comprises supplying said first and second MP gas stream each at least in part to said MP condensation section.

The urea production plant may e.g. be a grass-roots plant but may also be obtained e.g. by modifying an existing plant.

The invention pertains to a method of modifying an existing urea plant of the $CO_2$ stripping type by adding the MP treatment unit, the MP dissociator, and the MP carbamate condenser.

The invention also pertains to a method of modifying an existing urea plant of the $CO_2$ stripping type and already comprising an MP dissociator and an MP carbamate condenser, by adding the MP treatment unit downstream of the HP stripper.

The invention also pertains to a method of modifying an existing plant for producing a urea-containing product. The existing plant comprises for example a urea production section comprising a high pressure (HP) synthesis section comprising a HP stripper, a reactor for forming urea from $NH_3$ and $CO_2$, and a HP carbamate condenser, wherein the reactor and the HP carbamate condenser are optionally combined, wherein the HP stripper has an inlet for $CO_2$ feed as strip gas. The existing plant also typically comprises a HP $CO_2$ compressor. The method comprises for instance adding, if not already present in the existing plant, an MP dissociator and an MP condensation section, and a connection from the outlet for a urea synthesis solution to the MP dissociator, and a gas flow line for a second MP gas stream from the MP dissociator to the MP condensation section. The method furthermore comprises adding to the plant a medium pressure (MP) treatment unit, preferably an MP adiabatic flash vessel, and a liquid flow line for stripped urea solution from said HP stripper to said MP treatment unit, a gas flow line for a first MP gas stream from the MP treatment unit to the MP condensation section.

Optionally the method furthermore involves adding the optional MP stripper of the plant. In an advantageous embodiment, the method involves adding a dedicated $CO_2$ compressor to the existing plant for compressing $CO_2$ to MP and having an outlet for $CO_2$ connected to a gas flow line directly or indirectly to the MP carbamate condenser. In this embodiment advantageously the plant capacity can be increased without increasing or modifying the HP $CO_2$ compressor.

The discussed revamping methods (methods of modifying an existing plant) preferably give the inventive plant as discussed. Preferences for the inventive plant also apply for the method of modifying an existing plant. Details for the units described in connection with the plant also apply to the units used or added in the method of modifying an existing plant. The connection of the liquid outlet from the MP carbamate condenser to the HP synthesis section may involve adding a HP carbamate pump. The method may also involve installing an after-reactor to effectively enlarge the reactor volume.

Figure 1:
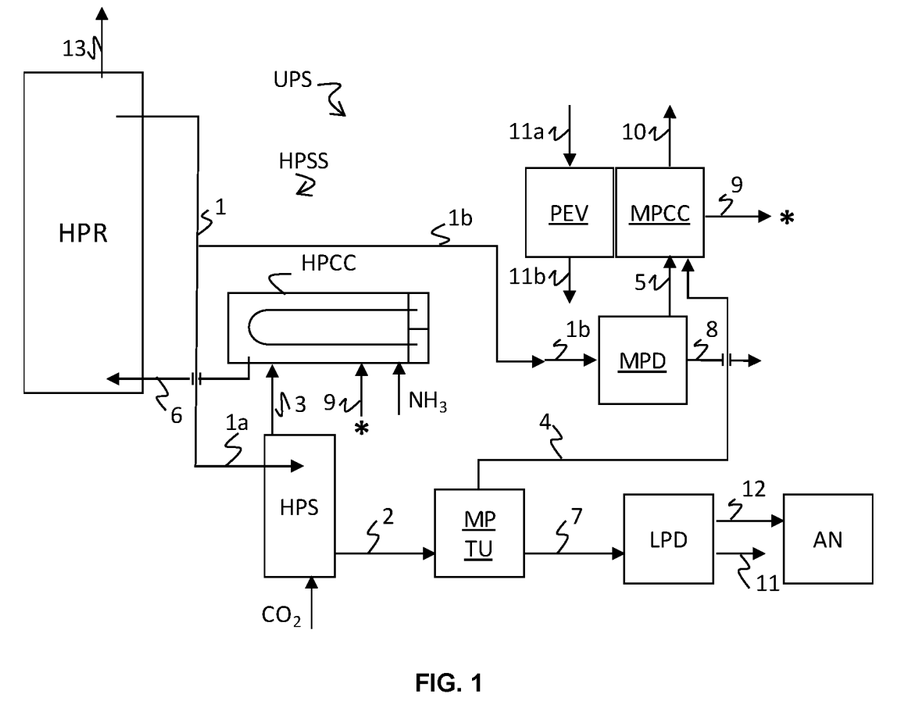
FIG. 1 schematically illustrates an example plant and process according to the invention.

FIG. 1 schematically illustrates an example embodiment of a process and plant according to the invention.

The plant comprises a urea production section (UPS) comprising a high pressure (HP) synthesis section (HPSS), which HP section comprises a HP stripper (HPS), a reactor (HPR) for forming urea from $NH_3$ and $CO_2$, in particular a HP urea reactor, and a HP carbamate condenser (HPCC). The HP stripper has an inlet for $CO_2$ feed as strip gas. The reactor and the HP carbamate condenser are optionally combined in a single vessel. The HP carbamate condenser (HPCC) is merely as an example schematically illustrated as a horizontal submerged condenser. Optionally already some urea formation takes place in the HP carbamate condenser (HPCC). The HP synthesis section, e.g. the HP carbamate condenser, comprises an inlet for $NH_3$ feed.

The urea production section further comprises a medium pressure (MP) treatment unit (MPTU), an MP dissociator (MPD) and an MP condensation section (MPCC). The HP urea reactor has an outlet for a urea synthesis solution (1) connected to a first liquid flow line (1a) to the HP stripper, and a second liquid flow line (1b) to the MP dissociator (MPD).

The urea production section comprises a liquid flow line for stripped urea solution (2) from the HP stripper (HPS) to the MP treatment unit (MPTU), a gas flow line for a gas stream (3) from the HP stripper, a gas flow line for a first MP gas stream (4) from the MP treatment unit (MPTU) to the MP condensation section (MPCC), and a gas flow line for a second MP gas stream (5) from the MP dissociator (MPD) to the MP condensation section (MPCC).

The gas (3) from the HP stripper is sent to the HP carbamate condenser (HPCC) where it is condensed. A carbamate-containing stream (6) is supplied to the reactor. The MP treatment unit (MPTU) has an outlet (7) for first MP urea solution. The MP dissociator (MPD) has an outlet (8) for second MP urea solution. The MP condensation section (MPCC) has an outlet for MP carbamate solution (9) and an outlet for gas (10). The MP condensation section (MPCC) has for instance a heat exchanging wall in heat-exchanging contact with an optional pre-evaporator (PEV) used for heating a urea solution (11a) to remove water from that solution. The concentrated urea solution (11b) is for instance supplied to an optional finishing section for producing solid urea.

Typically, as illustrated, the urea solution (7) from the MP treatment unit (MPTU) is supplied directly or indirectly to an LP dissociator (LPD) which can also be described as an LP thermal treatment unit and which is used for heating the solution. The LP dissociator (LPD) has an outlet for LP urea solution (11) and an outlet for LP gas (12). The LP gas is supplied for instance directly to indirectly to an ammonia-consuming unit, e.g. a neutralization section of an ammonium nitrate section (AN). The reactor for example has an outlet (13) for gas, which gas is e.g. also supplied to the neutralization section.

In an example method of modifying an existing plant, the MP treatment unit, the MP dissociator and the MP condensation section are added to the existing plant, as well as the pre-evaporator. The respective flow connections are added as well.

Figure 2:
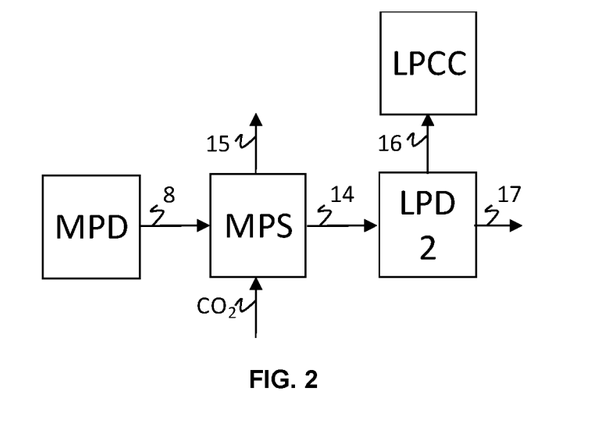
FIG. 2 schematically illustrates a detail of an example plant and process according to the invention.

FIG. 2 schematically illustrates an example embodiment of a process and plant according to the invention, with an optional MP stripper (MPS). The MP optional stripper receives urea solution (8) from the MP dissociator (MPD) and has an inlet for $CO_2$ strip gas, typically an MP $CO_2$ gas stream, for example the as first MP gas stream (4) and/or gaseous MP $CO_2$ feed. The gaseous MP $CO_2$ feed is optionally used in addition to the HP $CO_2$ feed to the HP stripper. The optional MP stripper (MPS) has an outlet for gas stream (15) connected to the MP condensation section (MPCC) and an outlet (14) for urea solution connected to an LP dissociation unit (LPD-2). The optional MP stripper (MPS) may also receive the first MP gas stream (4). The LP dissociation unit typically has an outlet (16) connected to gas flow line to an LP carbamate condenser, as well as an outlet (17) for LP urea solution. In an alternative embodiment, the gas outlet (16) is connected with the neutralization section of an ammonium nitrate section (AN).

In this application, for process streams (i.e. not for steam lines), high pressure (HP) is above 100 bar, for instance 120 to 300 bar, typically 150 to 200 bar. Medium pressure (MP) is for example 10 to 70 bar (including intermediate pressure of 30 to 70 bar), in particular 10 to 40 bar, and low pressure (LP) is for example 1.0 to 10 bar, in particular 1.0 to 8 bar, e.g. 1.5 to 5 bar. All pressures are in bar absolute.

The N/C ratio i.e. molar ratio $NH_3$ to $CO_2$ as used herein for the reactor reflects the composition of the so-called initial mixture before urea production, consisting only of $NH_3$, $CO_2$ and $H_2O$, as used in the art of urea plants. In particular, the N/C ratio for the reaction zone reflects the composition of the so-called initial mixture before urea production, consisting only of $NH_3$, $CO_2$ and $H_2O$, measured at the reactor outlet, as the term is conventionally used in the art. The N/C ratio for carbamate condensers is the molar ratio $NH_3$ to $CO_2$ measured at the outlet for carbamate solution. The N/C ratio for gas streams is the molar ratio $NH_3$ to $CO_2$. The N/C ratio for urea solutions downstream of the HP synthesis section is the molar ratio $NH_3$ to $CO_2$ of the actual mixture on the basis of carbamate converted to corresponding amounts of $NH_3$ and $CO_3$, i.e. not taking into account the urea component.

The term 'carbamate' as used herein refers to ammonium carbamate, as conventionally used in the art of urea plants.

The term 'typical' and 'in particular' are used to indicate features that can be used in some embodiments but that are not mandatory. Also preferred features are not mandatory.

The term "liquid communication" and the term "liquid flow line" refers to a flow line (e.g. tubing or ducts) allowing for passage of liquid between two units, optionally through a number of intermediate units. Liquid communication (and a liquid flow line) does not involve gas phase transport, and hence two units that are connected by an evaporator, a flow line for vapor, and a condenser are not in liquid communication (are not connected by a liquid flow line), although they are in fluid communication (which encompasses both gas phase transport and liquid transport). A first unit is in liquid communication with a second unit for instance if the outlet for liquid of the first unit is connected with an inlet of a condenser and an outlet for liquid of the condenser is connected with an inlet of the second unit.

The stripper efficiency (alpha) is defined as the amount of ammonia converted to urea (and biuret) divided by the total amount of ammonia, typically measured at the liquid outlet of the stripper. This definition is equivalent to that of the $NH_3$ conversion based on the outlet of the stripper. Hence, alpha=(2*wt. % urea/60)/((2*wt. % urea/60)+(wt. % $NH_3$/17)), measured at the liquid outlet of the stripper, wherein wt. % $NH_3$ includes all ammonia species including ammonium carbamate. The skilled person understands that "stripping efficiency" refers to the urea purity at the stripper liquid outlet and not to the energy efficiency of the stripper.

Condensation in a carbamate condenser refers to so-called carbamate condensation, which involves the reaction of $NH_3$ and $CO_2$ into ammonium carbamate which is a liquid, such that in effect gaseous $NH_3$ and $CO_2$ become carbamate in a liquid phase. Carbamate decomposition refers to the dissociation reaction of carbamate into $NH_3$ and $CO_2$.

The term 'shell space' as used herein refers to the shell side space of a shell-and-tube heat exchanger.

Preferences indicated for the inventive plant apply also for the inventive revamping method and for the process. The inventive urea production process is preferably carried out in the inventive plant. The integrated process is preferably carried out in the integrated plant. The inventive revamping method preferably gives the inventive plant(s) as the modified plant.

Some embodiments of the disclosure pertain to a plant and a process for producing a urea-containing product. The plant comprises a medium pressure dissociation unit and a high pressure $CO_2$ stripper each receiving a part of the urea synthesis solution. Stripped urea solution is further treated in a medium pressure treatment unit.

Example 1

In a urea plant according to the invention, in particular according to FIG. 2 however with the gas outlet (16) connected with the neutralization section of an ammonium nitrate section (AN), 34,000 kg/hour $CO_2$ was supplied to the HP stripper, 4,000 kg/hr gaseous MP $CO_2$ stream to the MP stripper (MPS) and for the larger part via the stream (15) to the MP condensation section (MPCC), and 7,000 kg/hr $CO_2$ was removed from the stripped urea solution (2) in the MP treatment unit (MPTU), being an MP adiabatic flash vessel, and supplied as first MP gas stream (4) from the MP treatment unit (MPTU) to the MP stripper (MPS). Thereby $CO_2$ was completely condensed in the MP condensation section (MPCC). $CO_2$ emissions from the ammonium nitrate section (AN) were reduced with 7,000 kg/hr $CO_2$ and advantageous urea concentration was achieved in the pre-evaporator (PEV).

The invention claimed is:

1. A plant for producing a urea-containing product, the plant comprising a urea production section comprising a high pressure (HP) synthesis section comprising a HP stripper, a reactor for forming urea from $NH_3$ and $CO_2$, and a HP carbamate condenser, the urea production section further comprising a medium pressure (MP) treatment unit, an MP dissociator and an MP condensation section,
   wherein the reactor has an outlet for a urea synthesis solution connected to a first liquid flow line connected to the HP stripper, wherein said outlet is also connected to a second liquid flow line connected to the MP dissociator, wherein the second liquid flow line bypasses the HP stripper,
   wherein the HP stripper has an inlet for $CO_2$ feed as strip gas,
   wherein the plant comprises a liquid flow line for stripped urea solution from said HP stripper to said MP treatment unit, a gas flow line for a first MP gas stream from the MP treatment unit to the MP condensation section, and a gas flow line for a second MP gas stream from the MP dissociator to the MP condensation section.

2. A plant according to claim 1, wherein the MP treatment unit and the MP dissociator are arranged in parallel.

3. A plant according to claim 1, wherein the MP dissociator is a heat exchanger using steam as a heating fluid.

4. A plant according to claim 1, wherein the plant further comprises an ammonium nitrate section comprising a neutralization section configured for neutralizing nitric acid with ammonia to form ammonium nitrate and having an inlet for nitric acid and an inlet for ammonia-containing gas from a unit comprised in said urea production section downstream of an outlet for urea solution of the MP treatment unit, wherein the plant further comprises a low pressure (LP) dissociator and a liquid flow line for MP urea solution from the MP treatment unit to said LP dissociator and a gas flow line for ammonia-containing LP gas from said LP dissociator to said neutralization section.

5. A plant according to claim 4, wherein the plant further comprises a liquid flow line from said MP dissociator to said LP dissociator or to an additional LP dissociator, said additional LP dissociator having an outlet for LP urea solution and an outlet for a second ammonia-containing LP gas stream connected to said neutralization section.

6. A plant according to claim 4, wherein said MP treatment unit comprises an MP flash vessel receiving said stripped urea solution and having an outlet for said first MP gas stream and an outlet for MP urea solution.

7. A plant according to claim 1, wherein a liquid outlet for carbamate solution of said MP condensation section is connected to a recycle flow line to said HP synthesis section.

8. A plant according to claim 1, wherein said plant comprises a pre-evaporator for removing water from a urea solution, wherein said MP condensation section comprises a heat exchanging wall for exchanging heat with said pre-evaporator,
   wherein the plant comprises a shell-and-tube heat exchanger having a tube side and a shell side wherein the tube side provides the pre-evaporator and wherein the shell side provides at least a part of the MP condensation section.

9. A plant according to claim 1, wherein said plant comprises a split of a flow line for HP urea synthesis solution into said first liquid flow line and said second liquid flow line.

10. A plant according to claim 9, wherein the split comprises a valve.

11. The plant according to claim 1, wherein the reactor and the HP carbamate condenser are combined.

12. A plant according to claim 1, wherein said MP treatment unit comprises an MP flash vessel, wherein the MP flash vessel receives said stripped urea solution and has a gas outlet for said first MP gas stream and a liquid outlet for MP urea solution.

13. A plant according to claim 12, further comprising an MP stripper for subjecting the urea solution from the MP dissociator to counter-current direct contact with the first MP gas stream from the MP treatment unit.

14. A plant according to claim 13, wherein the MP stripper is configured for adiabatic stripping.

15. A plant according to claim 13, wherein the plant comprises a liquid flow line from said MP stripper to an additional LP dissociator, wherein said additional LP dissociator has a liquid outlet for LP urea solution and a gas outlet for a second ammonia-containing LP gas stream connected to a low pressure carbamate condenser.

16. A plant according to claim 15, wherein the urea solution from the MP flash vessel is treated in an LP dissociator giving LP urea solution and ammonia-containing LP gas that is supplied to an ammonia-consuming unit, for example to an ammonium nitrate plant.

17. A process for producing a urea-containing product carried out in a plant according to claim 16, the process comprising:
   reacting $NH_3$ feed and $CO_2$ feed in said reactor, to give a urea synthesis solution;
   dividing said urea synthesis solution in at least a first part and a second part;
   supplying said first part to said HP stripper thereby obtaining stripped urea solution;
   subjecting said stripped urea solution to treatment at medium pressure in said MP treatment unit giving said first MP gas stream;
   subjecting said second part to medium pressure dissociation in said MP dissociator to give said second MP gas stream and MP urea solution, and
   supplying said first and second MP gas stream at least in part to said MP condensation section.

18. The process according to claim 17, wherein $NH_3$ and $CO_2$ are removed from said stripped urea solution in said MP treatment unit in a molar ratio of $NH_3$ to $CO_2$ of less than 2.0.

19. The process according to claim 17, wherein said treatment in said MP treatment unit involves substantially adiabatic flashing of the stripped urea solution to give said first MP gas stream.

20. The process according claim 17, comprising subjecting urea solution received directly or indirectly from said MP treatment unit to low pressure dissociation to give LP urea solution and ammonia-containing LP gas and using said ammonia-containing LP gas for neutralizing nitric acid to form ammonium nitrate.

21. A method of modifying an existing plant for producing a urea-containing product, wherein the existing plant comprises a urea production section comprising a high pressure (HP) synthesis section comprising a HP stripper, a reactor for forming urea from $NH_3$ and $CO_2$, and a HP carbamate condenser, wherein the HP stripper has an inlet for $CO_2$ feed as strip gas,
    wherein the method comprises adding:
        an MP dissociator and an MP condensation section, and a connection from the outlet for a urea synthesis solution to the MP dissociator bypassing the HP stripper, if not already present in the existing plant,
        a medium pressure (MP) treatment unit, and a liquid flow line for stripped urea solution from said HP stripper to said MP treatment unit, a gas flow line for a first MP gas stream from the MP treatment unit to the MP condensation section, and
        a gas flow line for a second MP gas stream from the MP dissociator to the MP condensation section, if not already present in the plant; thereby obtaining a plant according to claim 1.

22. A method of modifying an existing plant for producing a urea-containing product according to claim 21, wherein the reactor and the HP carbamate condenser are combined.

* * * * *